(12) United States Patent
Yokoyama et al.

(10) Patent No.: US 12,292,438 B2
(45) Date of Patent: May 6, 2025

(54) AUTOMATIC ANALYZER

(71) Applicant: Hitachi High-Tech Corporation, Tokyo (JP)

(72) Inventors: Koki Yokoyama, Tokyo (JP); Takenori Okusa, Tokyo (JP)

(73) Assignee: Hitachi High-Tech Corporation, Tokyo (JP)

(*) Notice: Subject to any disclaimer, the term of this patent is extended or adjusted under 35 U.S.C. 154(b) by 845 days.

(21) Appl. No.: 17/594,557

(22) PCT Filed: Feb. 25, 2020

(86) PCT No.: PCT/JP2020/007329
§ 371 (c)(1),
(2) Date: Oct. 22, 2021

(87) PCT Pub. No.: WO2020/235162
PCT Pub. Date: Nov. 26, 2020

(65) Prior Publication Data
US 2022/0187285 A1 Jun. 16, 2022

(30) Foreign Application Priority Data
May 17, 2019 (JP) ................................ 2019-093649

(51) Int. Cl.
*G01N 33/53* (2006.01)
*G01N 33/543* (2006.01)
(Continued)

(52) U.S. Cl.
CPC ... *G01N 33/5302* (2013.01); *G01N 33/54326* (2013.01); *G01N 35/1002* (2013.01); *G01N 2035/00425* (2013.01)

(58) Field of Classification Search
CPC ......... G01N 33/5302; G01N 33/54326; G01N 35/1002; G01N 2035/00425
See application file for complete search history.

(56) References Cited

U.S. PATENT DOCUMENTS

| 2015/0086164 A1 | 3/2015 | Nishimura et al. |
| 2021/0018522 A1 | 1/2021 | Yamashita et al. |

FOREIGN PATENT DOCUMENTS

| JP | 60-23725 Y | 7/1985 |
| JP | 6-34688 Y | 9/1994 |

(Continued)

OTHER PUBLICATIONS

Partial Supplementary European Search Report issued in European Application No. 20808285.9 dated May 25, 2023 (18 pages).
(Continued)

*Primary Examiner* — Brian J. Sines
(74) *Attorney, Agent, or Firm* — Crowell & Moring LLP

(57) ABSTRACT

Provided is an automatic analyzer to control a temperature of a reagent supplied to a magnetic separator with high accuracy. The automatic analyzer includes a magnetic separator that separates a magnetic component and a non-magnetic component from liquid obtained by reacting a sample with a first reagent, a storage unit that accommodates a second reagent, a pipe used to supply the second reagent to the magnetic separator, and a heat exchanger that adjusts a temperature around the pipe. It is preferable that the heat exchanger includes a heat absorption and dissipation unit and a fan that blows air heat-exchanged by the heat absorption and dissipation unit, and the air blown from the fan is blown onto the pipe.

12 Claims, 6 Drawing Sheets

(51) Int. Cl.
*G01N 35/00* (2006.01)
*G01N 35/10* (2006.01)

(56) References Cited

FOREIGN PATENT DOCUMENTS

| | | |
|---|---|---|
| JP | 6-300760 A | 10/1994 |
| JP | 2015-64448 A | 4/2015 |
| JP | 2017-026469 A | 2/2017 |
| WO | WO 2019/087482 A1 | 5/2019 |

OTHER PUBLICATIONS

English translation of document C3 (International Preliminary Report on Patentability (PCT/IPEA/409), filed on Oct. 22, 2021, issued in PCT Application No. PCT/JP2020/007329 dated May 12, 2021 (6 pages).
International Search Report (PCT/ISA/210) issued in PCT Application No. PCT/JP2020/007329 dated Apr. 21, 2020 with English translation (four (4) pages).
Japanese-language Written Opinion (PCT/ISA/237) issued in PCT Application No. PCT/JP2020/007329 dated Apr. 21, 2020 (four (4) pages).
International Preliminary Report on Patentability (PCT/IB/338 & PCT/EPEA/409) issued in PCT Application No. PCT/JP2020/007329 dated May 12, 2021 (four (4) pages).

[FIG. 1]
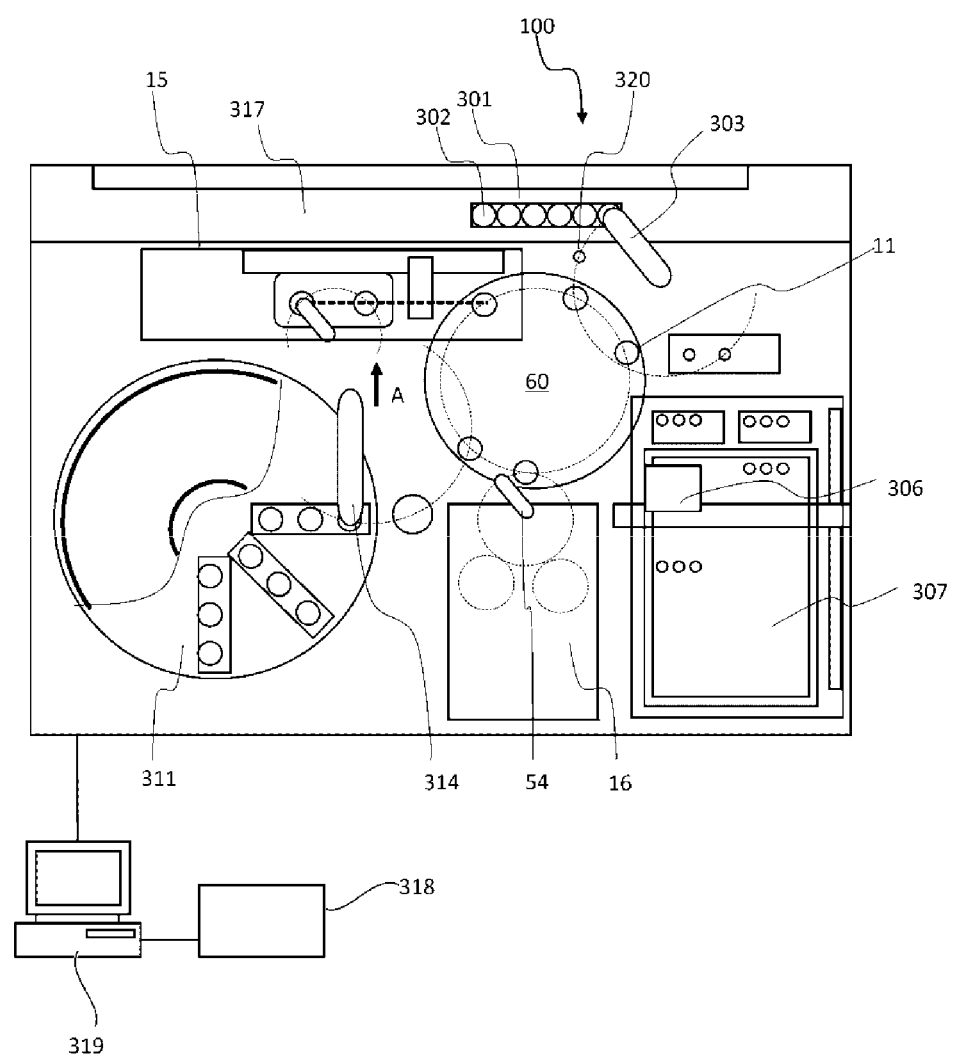

[FIG. 2]
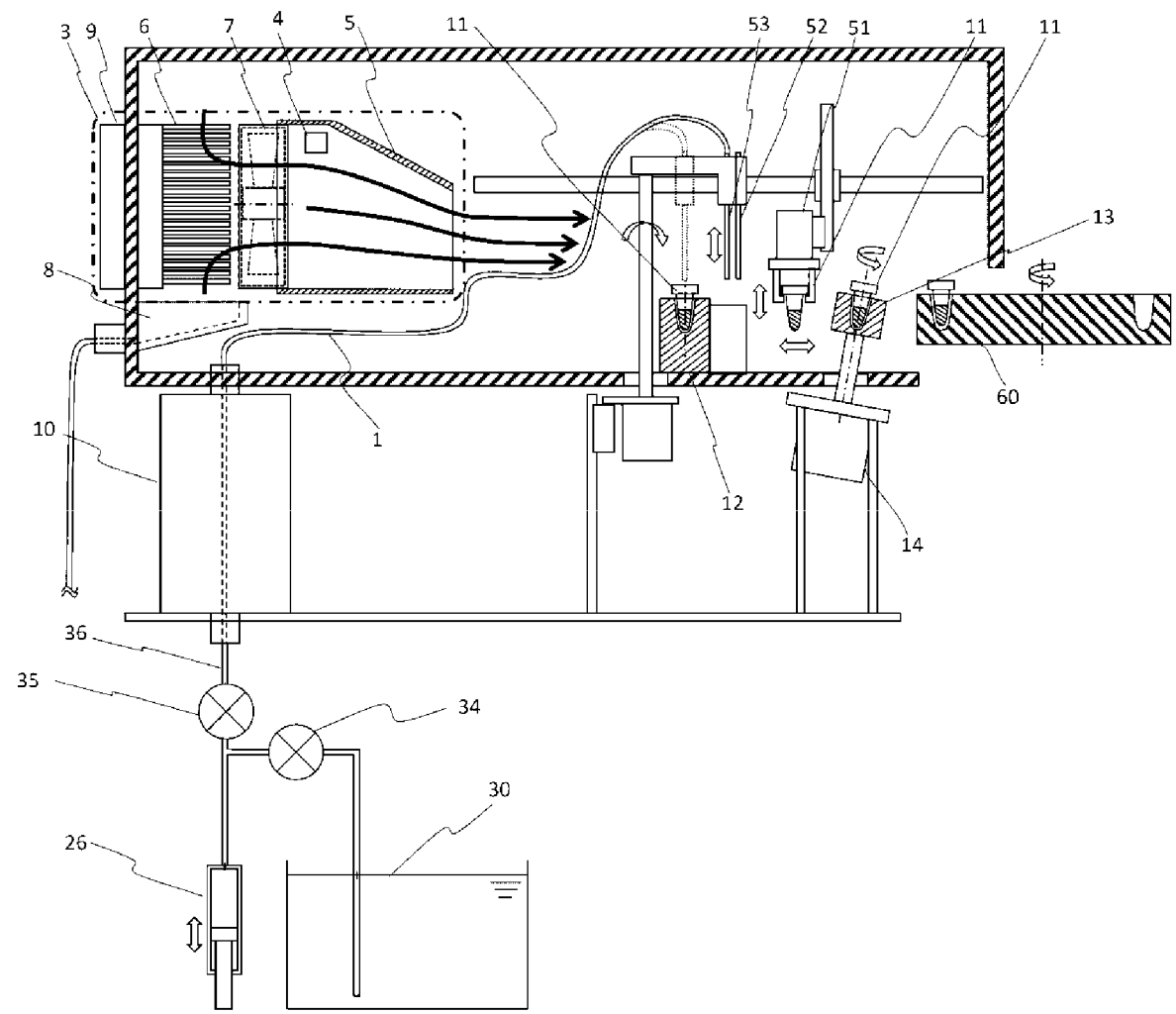

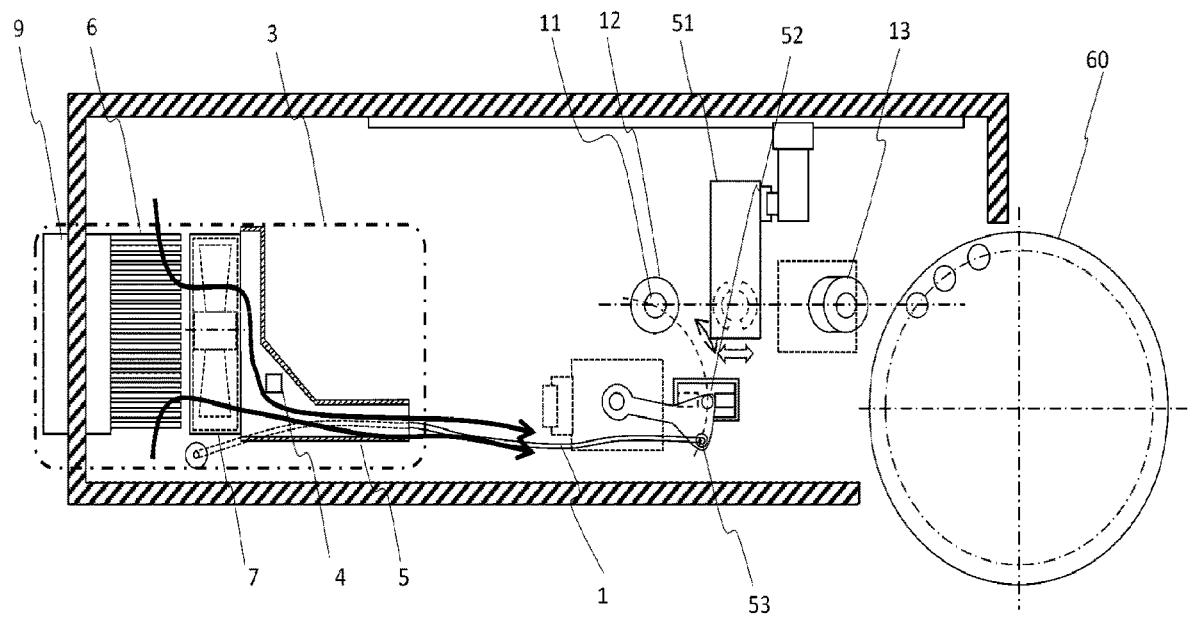
[FIG. 3]

[FIG. 4]
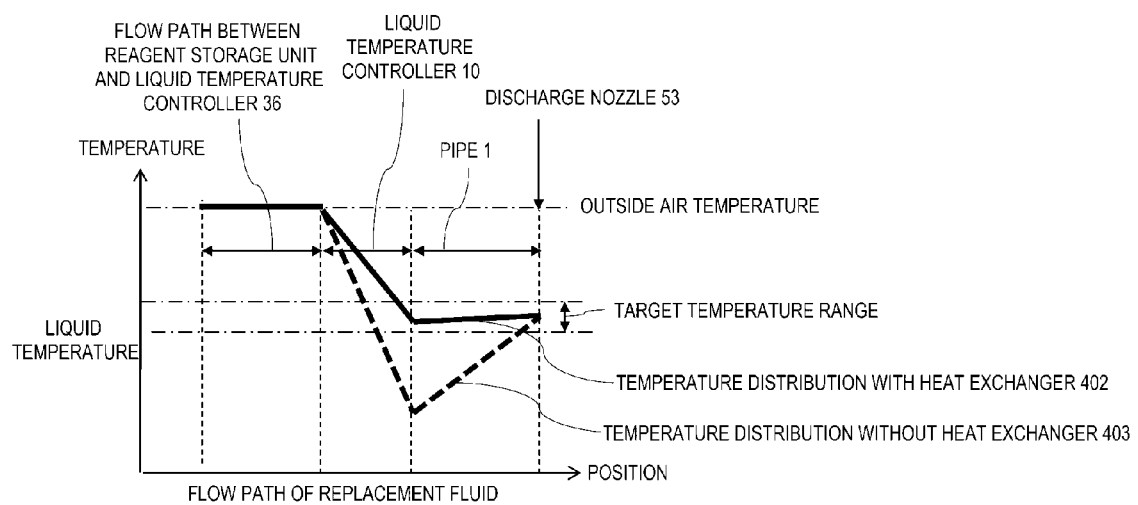

[FIG. 5]
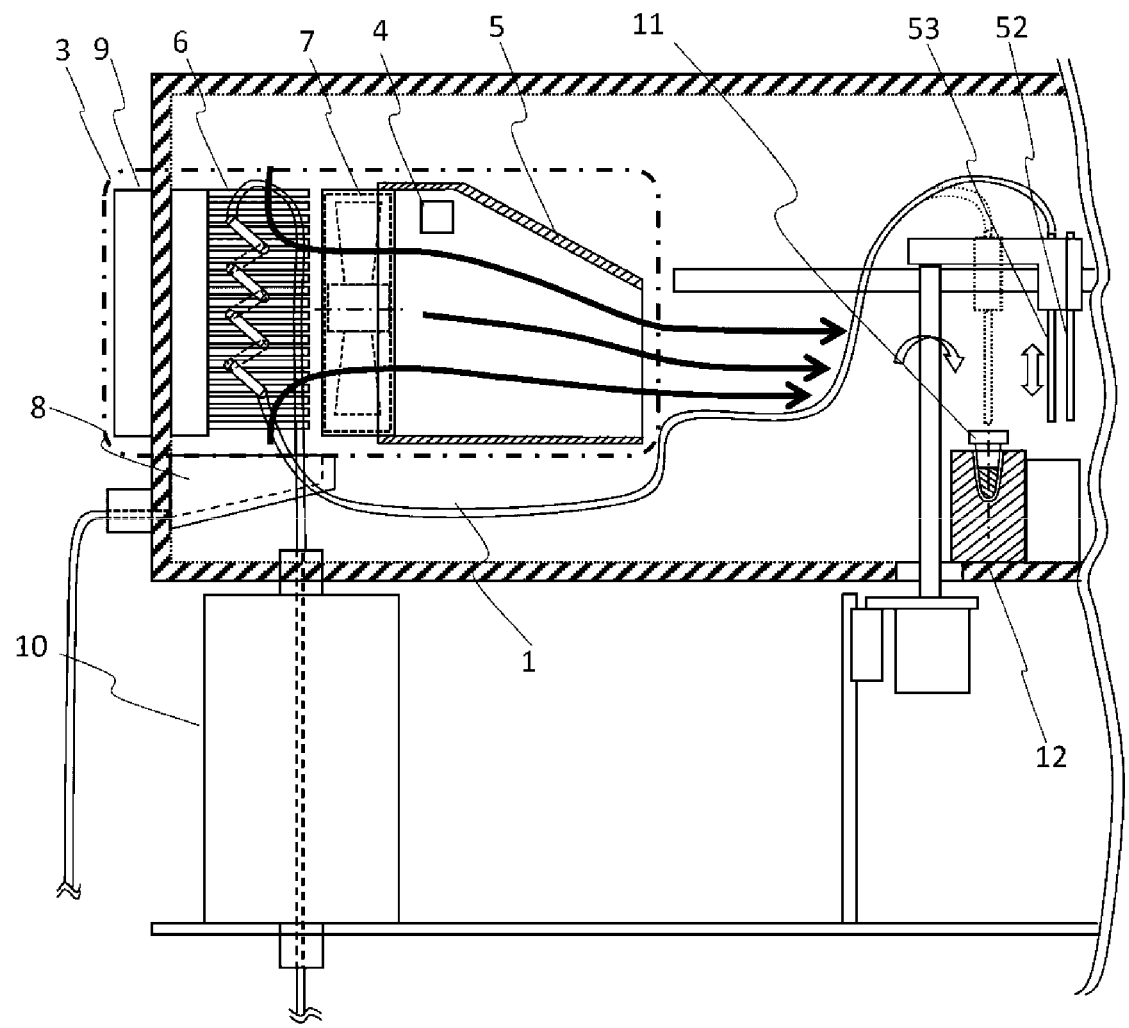

[FIG. 6]
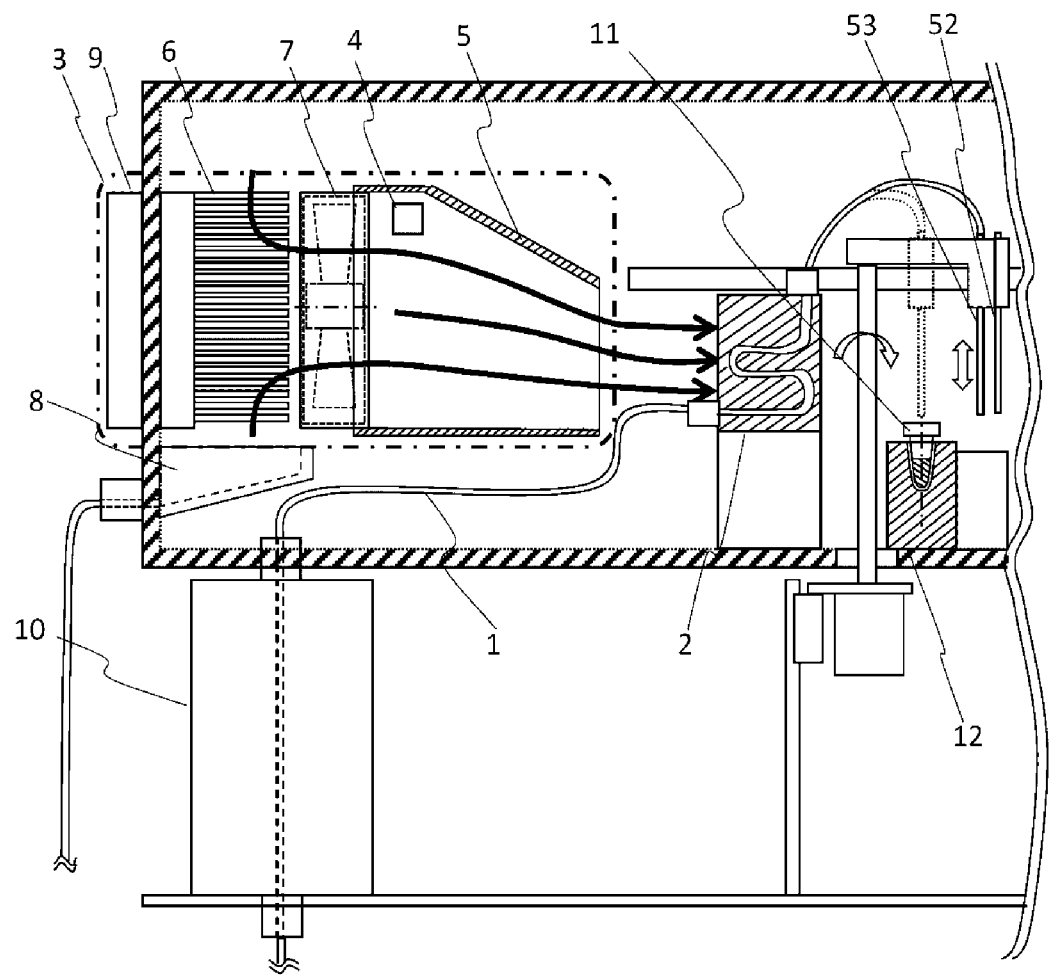

AUTOMATIC ANALYZER

TECHNICAL FIELD

The present invention relates to an automatic analyzer.

BACKGROUND ART

In an immunoassay method using an immune reaction, a substance to be measured and a labeling substance are bound to each other through antigen-antibody reaction, and the substance is quantitatively or qualitatively measured by signals such as light emission and absorption obtained from the labeling substance. In this case, in order to remove excessively added labeling substance, an operation called bound/free (B/F) separation is performed to remove labeling substance that is not bound to a target substance.

In an automatic analyzer, a method using magnetic particles is widely adopted to automatically perform the B/F separation. In the B/F separation using the magnetic particles, the B/F separation is performed by further binding the magnetic particles to an immune complex in which the substance to be measured and the labeling substance are bound, and adsorbing the magnetic particles with a magnet. The excess labeling substance is removed from reaction liquid by replacing a solution in a B/F separation state or the like.

Such B/F separation is used at the time of sample detection, sample pretreatment, etc. In the pretreatment, liquid in a reaction vessel is replaced in the B/F separation state, and the reaction liquid is washed. In order to maintain a washing reproducibility of the B/F separation for each analysis, it is desirable that a temperature of replacement fluid used in washing is constant. As a technique for controlling the temperature of the replacement fluid, PTL 1 below describes that a temperature of a replacement fluid tank that stores the replacement fluid is controlled to be constant regardless of an outside air temperature by using a liquid temperature controller such as a Peltier element.

CITATION LIST

Patent Literature

PTL 1: JP-A-2017-26469

SUMMARY OF INVENTION

Technical Problem

Considering miniaturization and improvement of processing capacity of the automatic analyzer, the liquid temperature controller is not always installed near a supply port of the replacement fluid. In that case, it is necessary to connect the liquid temperature controller to a magnetic separator, which is the supply port of the replacement fluid, with a pipe.

However, when the replacement fluid flows through the pipe, the temperature of the replacement fluid at the time of supply may change due to the outside air or exhaust heat from a motor, etc. Moreover, when the replacement fluid is supplied intermittently, the replacement fluid stays in the pipe for a long time, and the liquid temperature at the time of supply is also easily influenced.

An object of the invention is to provide an automatic analyzer that controls a temperature of a reagent supplied to a magnetic separator with high accuracy.

Solution to Problem

In order to solve the above problem, the invention is an automatic analyzer, including: a magnetic separator that separates a magnetic component and a non-magnetic component from liquid obtained by reacting a sample with a first reagent; a storage unit that accommodates a second reagent; a pipe used to supply the second reagent to the magnetic separator; and a heat exchanger that adjusts a temperature around the pipe.

Effect of Invention

According to the invention, an automatic analyzer that controls a temperature of a reagent supplied to a magnetic separator with high accuracy is provided.

BRIEF DESCRIPTION OF DRAWINGS

FIG. 1 is a plan view showing an overall configuration of an automatic analyzer.

FIG. 2 is a side view showing a schematic configuration of a processing unit viewed from a direction of an arrow A in FIG. 1 according to a first embodiment.

FIG. 3 is a plan view showing a schematic configuration of the processing unit.

FIG. 4 shows an example of temperature distribution on a flow path of replacement fluid.

FIG. 5 is a side view showing a schematic configuration of a processing unit viewed from the direction of the arrow A in FIG. 1 according to a second embodiment.

FIG. 6 is a side view showing a schematic configuration of a processing unit viewed from the direction of the arrow A in FIG. 1 according to a third embodiment.

DESCRIPTION OF EMBODIMENTS

Embodiments of the invention will be described in detail with reference to the drawings.

First Embodiment

An automatic analyzer of the present embodiment will be described with reference to FIGS. 1 to 4.

First, an outline of an overall configuration of the automatic analyzer according to the present embodiment will be described with reference to FIGS. 1 to 3. FIG. 1 is a plan view showing an overall configuration of the automatic analyzer according to the present embodiment. FIG. 2 is a side view showing a schematic configuration of a processing unit 15 in FIG. 1 as viewed from a direction of an arrow A. FIG. 3 is a plan view showing a schematic configuration of the processing unit 15.

As shown in FIG. 1, an automatic analyzer 100 in the present embodiment is a device that performs a reaction between a sample and a reagent and measures reacted reaction liquid. The automatic analyzer 100 includes a sample dispensing nozzle 303, a reaction table 60, a reaction vessel transport mechanism 306, a sample dispensing tip and reaction vessel holding member 307, a reagent disk 311, a reagent dispensing nozzle 314, the processing unit 15, a detector 16, a rack transport line 317, and a control device 319.

The rack transport line 317 is a line for transporting a rack 301, on which a plurality of sample containers 302 each accommodating the sample can be placed, to a sample dispensing position. The sample dispensing nozzle 303 is a nozzle for aspirating the sample accommodated in the sample containers 302 and discharging the sample to a reaction vessel 11. The reaction table 60 is a disk for performing the reaction between the sample and the reagent at a constant temperature, and the reaction between the sample and the reagent is promoted by keeping the temperature at a predetermined temperature by a heater (not shown). The reaction vessels 11 are held in plurality in the reaction table 60, and serve as a site where the sample and the reagent are mixed and reacted. The reaction vessel transport mechanism 306 transports the reaction vessels 11. The sample dispensing tip and reaction vessel holding member 307 stores a disposable sample dispensing tip used for sample dispensing and the reaction vessels 11. The reagent disk 311 is a disk for storing reagent bottles, and is kept cold in order to prevent deterioration of the reagent. The reagent dispensing nozzle 314 is a nozzle for aspirating the reagent stored in the reagent bottles in the reagent disk 311 and discharging the reagent to the reaction vessels 11. The reagent bottles in the reagent disk 311 accommodate various assay reagents (first reagent) used for sample analysis. The processing unit 15 performs processing before analysis of the sample by the detector 16. The detector 16 performs detection using the liquid in which the reaction is completed in the reaction vessel 11. Details of the processing unit 15 will be described below. The control device 319 controls various operations of each of the above members, and performs calculation processing for obtaining a concentration of a predetermined component in the sample from a detection result obtained by the detector 16. The control device 319 is provided with a temperature controller 318 that executes temperature control for the liquid temperature controller 10 and a heat exchanger 3.

Next, an outline of an overall analysis flow in the automatic analyzer according to the present embodiment will be described. Prior to the analysis, a user installs consumables such as the reagent bottle, the sample dispensing tip and the reaction vessels 11 necessary for the analysis on the reagent disk 311 and the sample dispensing tip and reaction vessel holding member 307 in the analyzer, respectively.

First, the user puts the rack 301 into the automatic analyzer in a state where the sample such as blood or urine to be analyzed is put into the sample containers 302. Here, unused reaction vessels 11 and the sample dispensing tip are transported to the reaction table 60 and a sample dispensing tip installation position by the reaction vessel transport mechanism 306 of the analyzer.

Thereafter, the reagent dispensing nozzle 314 accesses an inside of the reagent disk 311, so that the assay reagent stored in the reagent bottle is dispensed into the reaction vessels 11 on the reaction table 60.

Subsequently, when the rack 301 passes through the rack transport line 317 and reaches the sample dispensing position, the sample is dispensed into the reaction vessels 11 by the sample dispensing nozzle 303, and the reaction between the sample and the assay reagent is started. The reaction referred to herein means, for example, using a luminescence labeling antibody that reacts only with a specific antigen of the sample as the assay reagent to bind the sample and a luminescence labeling substance by an antigen-antibody reaction. In this case, the sample and the assay reagent are stirred by aspirating and discharging the mixture of the sample and the assay reagent in the sample dispensing tip. After this operation is completed, the used sample dispensing tip is discarded to a disposal outlet 320.

After the reaction between the sample and the assay reagent is started by stirring, another reagent may be further added at a specific timing to perform the reaction. For example, there is a process of further binding, to the antigen described above, magnetic beads bound with an antibody to a surface thereof. For this purpose, the reaction vessels 11 placed on the reaction table 60 for a predetermined time are transported by a first transport mechanism 51 to the magnetic separator 12 in the processing unit 15 that pretreats the analysis.

As shown in FIG. 2, in the magnetic separator 12, magnetic separation of the sample is performed, then unnecessary solution is discharged from an aspiration nozzle 52, and a reagent called replacement fluid is discharged from a discharge nozzle 53. The replacement fluid is a second reagent used for washing as a system reagent different from the above assay reagent, and is stored in the reagent storage unit 30. The replacement fluid is supplied by opening an electromagnetic valve 34 and closing an electromagnetic valve 35 to aspirate the reagent into a syringe pump 26 that intermittently feeds the reagent, then closing the electromagnetic valve 34 and opening the electromagnetic valve 35 to discharge the reagent from the syringe pump 26. The temperature of the replacement fluid is adjusted in advance by the liquid temperature controller 10. After being adjusted by the liquid temperature controller 10, the replacement fluid passes through a pipe 1 and is supplied to the discharge nozzle 53. The aspiration nozzle 52, the discharge nozzle 53, the reagent storage unit 30, the electromagnetic valves 34 and 35, the syringe pump 26, and the pipe 1 correspond to supply equipment for supplying the reagent to the reaction vessel 11 installed in the processing unit 15.

After the magnetic separation process is completed, the reaction vessel 11 is transported to a stirrer 13 in the processing unit 15 by the first transport mechanism 51. In the stirrer 13, stirring is performed by rotating the reaction vessel 11 by a motor 14.

After the stirring for a predetermined time is completed, the reaction vessel 11 is transported to the reaction table 60 again by a second transport mechanism 54.

Regardless of presence or absence of the magnetic separation, the reaction vessel 11 placed on the reaction table 60 for the predetermined time is guided to the detector 16 by the second transport mechanism 54. The detector 16 detects a signal from the reaction liquid, notifies the user of an analysis result, and records the analysis result in a memory device.

After a detection operation is completed, the reaction vessel 11 is transported to the disposal outlet 320 by the second transport mechanism 54 and the reaction vessel transport mechanism 306, and is discarded.

Next, the temperature control for the replacement fluid will be described in detail in the present embodiment.

The temperature of the reagent or reaction liquid in the automatic analyzer needs to be controlled within a certain range regardless of the outside air temperature in order to maintain the reproducibility of each measurement. However, different steps may have the same required target temperatures, but different temperature accuracies. For example, the temperature of the replacement fluid, the liquid temperature at the time of magnetic separation, and the liquid temperature at the time of stirring by the stirrer 13 as a subsequent step have the same target temperature Ta. Meanwhile, a tolerable temperature accuracy varies in the above steps. That is, it is required that different steps are controlled with different temperature accuracies, such that the liquid temperature of the replacement fluid is controlled within TaΔ1 and the liquid temperatures at the time of the magnetic separation and stirring is within TaΔ2. In particular, the temperature of the replacement fluid also influences the temperatures at the time of the magnetic separation and stirring as subsequent steps, and thus requires highly accurate temperature control.

The replacement fluid is temperature-controlled by the liquid temperature controller 10 and then supplied to the reaction vessel 11 by the discharge nozzle 53, which is also one of the components constituting the magnetic separator 12. Here, an environment in which the automatic analyzer is used is assumed to be environments from higher than to lower than the above target temperature Ta. However, when the liquid temperature controller 10 and the discharge nozzle 53 are provided close to each other, the pipe 1 is as short as possible and is less susceptible to the environment. That is, the temperature difference between the replacement fluid at the outlet of the liquid temperature controller 10 and the replacement fluid when reaching the discharge nozzle 53 is small. Therefore, as long as the liquid temperature controller 10 is appropriately controlled, the temperature of the replacement fluid discharged from the discharge nozzle 53 can also be controlled with high accuracy.

However, considering the miniaturization and improvement of the processing capacity of the overall automatic analyzer, it is not always possible to arrange the liquid temperature controller 10 and the discharge nozzle 53 close to each other. When the pipe 1 is long and a large temperature difference exists between the outside air temperature and the target temperature, a heat influence of absorbing or dissipating heat from the outside air while the replacement fluid is passing through the pipe 1 cannot be ignored. In such a case, a temperature at which the replacement fluid is supplied to the magnetic separator 12 may deviate from the temperature accuracy of the target temperature.

In order to prevent the influence from the outside air while the replacement fluid is passing through the pipe 1, it is also possible to wrap a heat insulating material or the like on the surface of the resin pipe 1. However, when the heat insulating material or the like is wrapped around the pipe 1, the entire pipe 1 becomes thick and the movable ranges of the discharge nozzle 53 and the aspiration nozzle 52 are restricted, or the pipe 1 becomes difficult to bend and the degree of freedom when arranging each equipment is reduced.

Further, it is difficult for the liquid temperature controller 10 alone to control the temperature of the replacement fluid within the range of temperature accuracy with respect to the change in the outside air temperature for the following three reasons.

First, when the heat amount subjected to the heat exchange by the pipe 1 with the outside air is large, it is necessary to supply the replacement fluid while significantly changing a control temperature of the replacement fluid in the liquid temperature controller 10 with respect to the target temperature. For example, when the outside air temperature is 32° C. and the target temperature is 25° C., the temperature of the liquid temperature controller 10 is set to 18° C. In that case, dew condensation may occur on the surface of the pipe 1 or the liquid temperature controller 10, and dripping of dew condensation water on the reaction vessel or the like may influence the measurement accuracy.

Second, due to the configuration of the automatic analyzer, it is difficult to directly measure the temperature at the time of discharging the replacement fluid and feedback control the temperature. This is because not only a step of attaching a temperature sensor such as a thermistor or a thermoelectric pair is required, but also a wire of the temperature sensor may obstruct the flow of the reagent in the pipe 1.

Third, it is difficult to evaluate a relation between the outside air temperature and the discharged liquid temperature in a wide-range temperature band and determine a control constant of the liquid temperature controller 10. This is because when the heat amount subjected to the heat exchange by the pipe 1 changes due to the exhaust heat from the motor and the like, the relation between the outside air temperature and the discharge liquid temperature is not satisfied. As a tendency, when the temperature difference between the outside air temperature and the target temperature is large, there is a high possibility that the liquid temperature at the time of discharge will be out of the range of temperature accuracy.

Therefore, in the present embodiment, by providing the heat exchanger 3, the heat amount subjected to the heat exchange by the pipe 1 with the outside air is prevented, and the temperature difference between the replacement fluid at the outlet of the liquid temperature controller 10 and the replacement fluid when reaching the discharge nozzle 53 becomes small.

Next, arrangement of the heat exchanger 3 and the pipe 1 in the present embodiment will be described in detail.

The processing unit 15 of the present embodiment has the heat exchanger 3 that adjusts the temperature around the pipe 1. The heat exchanger 3 includes a heat absorption and dissipation unit 9, fins 6 that improve the efficiency of heat exchange with the air, a fan 7 that blows the heat exchanged air, and a rectifier 5 that rectifies the air in a direction in which the air is blown onto the pipe 1. The expression that the air blown from the heat exchanger 3 "is blown onto" the pipe 1 is not limited to a case where the air is directly blown onto the pipe 1, but also includes a case where the air is blown onto another object to indirectly reach the surface of the pipe 1.

The temperature of the blown air is detected by a temperature sensor 4. The temperature controller 318 controls the output of the heat absorption and dissipation unit 9 and the rotation speed of the fan 7 such that the temperature becomes the target temperature. Further, a drain pan 8 is provided to receive dropped dew condensation water when the temperature of the fins 6 in the heat exchanger 3 is lower than a dew point and dew condensation occurs.

A shape of the rectifier 5 is determined such that the temperature-controlled air is efficiently blown onto the surface of the pipe 1. In the present embodiment, the shape of the rectifier 5 is devised such that the pipe 1 is located in a flow path of the air blown from the heat exchanger 3 and substantially parallel to the flow path. As a result, a contact range between the temperature-controlled air and the pipe 1 is increased, and heat exchange between the temperature-uncontrolled outside air and the pipe 1 can be prevented. The pipe 1 may be provided with a spiral or U-shaped detour portion at the location at which the air blown from the fan 7 is blown to increase a heat transfer area with the temperature-controlled air. The fan 7 in the present embodiment is in a shape of an axial fan system in which the direction of rotation of the fan matches with the direction of wind, but also may be a centrifugal fan or the like in which the wind direction is 90° with respect to the rotation axis of the fan.

Next, an effect of the present embodiment will be described.

The temperature of the heat absorption and dissipation unit 9 is controlled such that the temperature of the air blown from the heat exchanger 3 is close to the target temperature of the replacement fluid. The temperature-controlled air is blown onto the surface of pipe 1, and thus it is possible to suppress the heat exchange between the replacement fluid whose temperature is controlled by the liquid temperature controller 10 and the outside air while moving in the pipe 1, and prevent the temperature change of the replacement fluid.

Therefore, even when the difference between the outside air temperature and the target temperature is large, the temperature of the replacement fluid can be controlled without significantly changing the temperature of the liquid temperature controller 10 with respect to the target temperature, as a result, it is possible to control the temperature of the replacement fluid discharged from the discharge nozzle 53 with high accuracy.

In the present embodiment, the temperature-controlled air by the heat exchanger 3 is blown to a downstream side of the pipe 1, that is, the pipe 1 on a side closer to the magnetic separator 12 than the liquid temperature controller 10, and thus the temperature of the replacement fluid can be accurately controlled at a position close to the discharge nozzle 53.

Next, arrangement of the pipe 1, the magnetic separator 12, and the stirrer 13 in the present embodiment will be described.

As shown in FIGS. 2 and 3, the pipe 1 is arranged at a position closest to the heat exchanger 3, and the discharge nozzle 53, the magnetic separator 12, and the stirrer 13 are arranged in this order so as to be closer to the heat exchanger. Therefore, airflow of the heat exchanger 3 first is blown onto the pipe 1, then the discharge nozzle 53, the magnetic separator 12, and finally the stirrer 13. Here, a supply temperature of the replacement fluid also influences the liquid temperatures at the time of magnetic separation and stirring, which are subsequent steps, and thus has a strictest accuracy of temperature control in the processing unit 15. Therefore, the temperature accuracy of the liquid temperature during stirring may be lower than that of the replacement fluid. In the present embodiment, the pipe 1 for supplying the replacement fluid, the discharge nozzle 53, the magnetic separator 12, and the stirrer 13 are arranged in a descending order of being strict in the accuracy of temperature control. The replacement fluid is close to the heat exchanger 3, and thus can be accurately controlled. Moreover, although the accuracy of the stirrer 13 is lower than that of the magnetic separator 12 or the like, the temperature can be controlled by the airflow of the heat exchanger 3. As a result, the temperatures of a plurality of temperature control targets can be controlled by one heat exchanger 3.

FIG. 4 is an explanatory diagram of an example schematically showing the temperature of the replacement fluid on the flow path from the reagent storage unit 30 to the discharge nozzle 53 in the pipe 1 according to the present embodiment. In the temperature distribution shown in FIG. 4, a vertical axis indicates the temperature of the replacement fluid on the flow path. A horizontal axis indicates the position of the flow path of the replacement fluid, and indicates a pipe 36 from the reagent storage unit to the liquid temperature controller, the liquid temperature controller 10, the pipe 1, and the discharge nozzle 53 from the left end. The temperature distribution shown by a solid line is temperature distribution 402 in a case "with" the heat exchanger 3 in the present embodiment, and the temperature distribution shown by a dotted line is temperature distribution 403 in a case "without" the heat exchanger 3 in the related art.

In the temperature distribution 403 in the case "without" the heat exchanger 3, it is necessary to significantly lower the temperature in the liquid temperature controller 10 in order to achieve the target temperature in the discharge nozzle 53. This is to prevent the temperature of the replacement fluid from rising due to heat exchange with the outside air while passing through the pipe 1 and deviating from the temperature accuracy of the target temperature. Meanwhile, in the temperature distribution 403 in the case "with" the heat exchanger 3, the target temperature can be achieved in the discharge nozzle 53 without significantly lowering the temperature of the liquid temperature controller 10. This is because the heat exchange with the outside air can be prevented by controlling the temperature around the pipe 1 by the airflow provided from the heat exchanger 3.

FIG. 4 shows a case where the target temperature is lower than the outside air temperature, but the same can be said in a case where the target temperature is higher than the outside air temperature. Basically, when the target temperature is lower than the outside air temperature, air absorbed and cooled by the heat absorption and dissipation unit 9 is blown, and when the target temperature is higher than the outside air temperature, air radiated and warmed by the heat absorption and dissipation unit 9 is blown. However, when the range in which the temperature can be controlled by the liquid temperature controller 10 is expanded, the control of the heat absorption and dissipation unit 9 is not limited to this.

Second Embodiment

FIG. 5 is a side view of a schematic configuration of the processing unit 15 when the pipe 1 is arranged differently from that of the first embodiment. In the present embodiment, as shown in FIG. 5, after passing through the fins 6 of the heat exchanger 3, the pipe 1 is connected to the discharge nozzle 53. According to the configuration, due to a layout of the automatic analyzer, even when the liquid temperature controller 10 and the discharge nozzle 53 are located far from each other and the pipe 1 is long, the heat transfer area in the heat exchanger 3 comes to be large and the temperature control by the heat exchanger 3 comes to be easy.

Third Embodiment

FIG. 6 is a side view of a schematic configuration of the processing unit 15 when the pipe 1 is arranged differently from that of the first and second embodiments. In the present embodiment, as shown in FIG. 6, the pipe 1 is covered with a heat transfer block 2 as a heat transfer member at the location onto which the temperature-controlled air by the heat exchanger is blown. The heat transfer block 2 has a spiral or U-shaped flow path formed inside in order to promote heat exchange with the airflow of the heat exchanger 3. A material of the heat transfer block 2 is preferably a metal material having a high thermal conductivity. In the present embodiment, the temperature control for the replacement fluid by the heat exchanger 3 comes to be easy as well.

The invention is not limited to the above embodiments, and includes various modifications. A part of a configuration of one embodiment can be replaced with a configuration of another embodiment, and the configuration of one embodiment may be added with the configuration of another embodiment. A part of the configuration of each embodiment may be added, deleted, or replaced with another configuration.

REFERENCE SIGN LIST 1 pipe
2 heat transfer block 3 heat exchanger
4 temperature sensor
5 rectifier
6 fin
7 fan
8 drain pan
9 heat absorption and dissipation unit
10 liquid temperature controller
11 reaction vessel
12 magnetic separator
13 stirrer
14 motor
15 processing unit
16 detector
26 syringe pump (supply device)
30 reagent storage unit (supply device)
34, 35 electromagnetic valve (supply device)
pipe between reagent storage unit and liquid temperature controller
51 first transport mechanism (heating element)
52 aspiration nozzle (supply device)
53 discharge nozzle (supply device)
54 second transport mechanism
60 reaction table
100 automatic analyzer
301 rack
302 sample container
303 sample dispensing nozzle
306 reaction vessel transport mechanism
307 sample dispensing tip and reaction vessel holding member
311 reagent disk
314 reagent dispensing nozzle
317 rack transport line
318 temperature controller
319 control device
320 disposal outlet
402 temperature distribution with heat exchanger
403 temperature distribution without heat exchanger

The invention claimed is:

1. An automatic analyzer, comprising:
a magnetic separator that separates a magnetic component and a non-magnetic component from liquid obtained by reacting a sample with a first reagent;
a storage unit that accommodates a second reagent;
a discharge nozzle that discharges the second reagent to a reaction vessel;
a pipe used to supply the second reagent to the discharge nozzle; and
a heat exchanger that adjusts a temperature around the pipe, wherein
the heat exchanger includes a rectifier configured to rectify heat-exchanged air,
a downstream end of the rectifier has a smaller cross-section than an upstream end of the rectifier,
the heat-exchanged air rectified by the rectifier is blown to the pipe, and
a space into which the heat-exchanged air is blown to and a tip of the discharge nozzle are in the same space.

2. The automatic analyzer according to claim 1, wherein the heat exchanger includes a heat absorption and dissipation unit and a fan that blows air heat-exchanged by the heat absorption and dissipation unit, and
the air blown from the fan is blown onto the pipe.

3. The automatic analyzer according to claim 2, further comprising:
a liquid temperature controller that controls a temperature of the second reagent, wherein
the air blown from the fan is blown onto a part of the pipe at a side closer to the magnetic separator than the liquid temperature controller.

4. The automatic analyzer according to claim 2, wherein the pipe at the part onto which the air blown from the fan is blown is covered with a heat transfer member.

5. The automatic analyzer according to claim 1, wherein the pipe is located substantially parallel to a flow path of the air rectified by the rectifier.

6. The automatic analyzer according to claim 1, wherein the pipe has a detour portion that increases a heat transfer area.

7. An automatic analyzer, comprising:
a magnetic separator that separates a magnetic component and a non-magnetic component from liquid obtained by reacting a sample with a first reagent;
a storage unit that accommodates a second reagent;
a discharge nozzle that discharges the second reagent to a reaction vessel;
a pipe used to supply the second reagent to the discharge nozzle; and
a stirrer that rotates liquid after separation in the magnetic separator, wherein
a heat exchanger is disposed at a position closest to the pipe among the pipe, the magnetic separator, a tip of the discharge nozzle, and the stirrer,
the heat exchanger includes a rectifier configured to rectify heat-exchanged air,
a downstream end of the rectifier has a smaller cross-section than an upstream end of the rectifier, and
the heat-exchanged air rectified by the rectifier is blown onto the pipe, the tip of the discharge nozzle, the magnetic separator, and the stirrer in this order.

8. An automatic analyzer, comprising:
a magnetic separator that separates a magnetic component and a non-magnetic component from liquid obtained by reacting a sample with a first reagent;
a storage unit that accommodates a second reagent;
a pipe used to supply the second reagent to the magnetic separator; and
a heat exchanger that adjusts a temperature around the pipe, wherein
the heat exchanger includes a fin, and
the pipe passes through the fin.

9. The automatic analyzer according to claim 8, wherein the heat exchanger includes a heat absorption and dissipation unit and a fan that blows air heat-exchanged by the heat absorption and dissipation unit, and
the air blown from the fan is blown onto the pipe.

10. The automatic analyzer according to claim 9, further comprising:
a liquid temperature controller that controls a temperature of the second reagent, wherein
the air blown from the fan is blown onto a part of the pipe at a side closer to the magnetic separator than the liquid temperature controller.

11. The automatic analyzer according to claim 9, wherein the pipe at the part onto which the air blown from the fan is blown is covered with a heat transfer member.

12. The automatic analyzer according to claim 8, wherein the pipe has a detour portion that increases a heat transfer area.

* * * * *